United States Patent
Renner

(10) Patent No.: US 8,605,857 B1
(45) Date of Patent: *Dec. 10, 2013

(54) METHOD AND SYSTEM TO RECONSTRUCT TREATMENT DOSE TO A PATIENT FROM INTEGRATED EXIT-TRANSIT IMAGES OF RADIATION FIELDS TAKEN DURING TREATMENT

(71) Applicant: Math Resolutions, LLC, Columbia, MD (US)

(72) Inventor: Wendel Dean Renner, Columbia, MD (US)

(73) Assignee: Math Resolutions, LLC, Columbia, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/736,003

(22) Filed: Jan. 7, 2013

Related U.S. Application Data

(63) Continuation-in-part of application No. 12/977,907, filed on Dec. 23, 2010, now Pat. No. 8,351,572.

(51) Int. Cl.
*A61N 5/10* (2006.01)

(52) U.S. Cl.
USPC .......................................................... 378/65

(58) Field of Classification Search
USPC ......... 378/62, 65, 64, 108; 382/128, 130–132
See application file for complete search history.

(56) References Cited

U.S. PATENT DOCUMENTS

| 5,754,622 | A * | 5/1998 | Hughes .......................... 378/65 |
| 6,438,202 | B1 * | 8/2002 | Olivera et al. .................. 378/65 |
| 6,636,622 | B2 * | 10/2003 | Mackie et al. ................ 382/132 |
| 2008/0049898 | A1 * | 2/2008 | Romesberg et al. ............ 378/65 |
| 2009/0003512 | A1 * | 1/2009 | Pouliot et al. ..................... 378/4 |
| 2010/0119032 | A1 * | 5/2010 | Yan et al. ............................ 378/4 |
| 2011/0013742 | A1 * | 1/2011 | Zaiki et al. ...................... 378/15 |

OTHER PUBLICATIONS

Wendell Dean Renner, Kevin Norton and Timothy Holmes, A Method for Deconvolution of Integrated Electronic Portal Images to Obtain Incident Fluence for Dose Reconstruction, Journal of Applied Clinical Medical Physics, vol. 6, No. 4, Fall 2005, pp. 22-39.*

Markus Wendling, Leah N. McDermo-I-F, Anton Mans, Jan-Jakob Sonke, Marcel van Herk, and Ben J. Mignheer, A Simple Backprojection Algorithm for 3D in vivo EPID Dosimetry of IMRT Treatments, Med. Phys. 36 (7), Jul. 2009, pp. 3310-3321.*

Markus Wendling, Robert J.W. Louwe, Leah N. McDermo-I-r, Jan-Jakob Sonke, Marcel van Herk, and Ben J. Mijnheer, Accurate Two-Dimensional IMRT Verification Using a Back-Projection EPID Dosimetry Method, Med. Phys. 33 (2), Feb. 2006, pp. 259-273.*

* cited by examiner

*Primary Examiner* — Irakli Kiknadze
(74) *Attorney, Agent, or Firm* — Rosenberg, Klein & Lee

(57) ABSTRACT

A method and system to compute the dose to a patient (2) given a captured integrated exit-transit image (5) of the radiation rays (4) traveling from the source of x-rays (1) through the patient (2) to the imaging device (3) to product the exit-transit image (5). Each radiation field image (5) is transformed (6,8,10,12) to multiple images (7,9,11,13) for each phantom thickness (26) that was measured with the imaging device (3) for a range of field sizes (21). Given the water equivalent path (22) through the patient for a ray (4) reaching a pixel (15, 16), the final pixel value (19) is interpolated from the images (9, 11) that bracket the water equivalent path through the patient (22).

20 Claims, 7 Drawing Sheets

US 8,605,857 B1

METHOD AND SYSTEM TO RECONSTRUCT TREATMENT DOSE TO A PATIENT FROM INTEGRATED EXIT-TRANSIT IMAGES OF RADIATION FIELDS TAKEN DURING TREATMENT

RELATED APPLICATION DATA

This application is a Continuation-In-Part of co-pending patent application Ser. No. 12/977,907, filed 23 Dec. 2010.

BACKGROUND OF THE INVENTION

1. Field of the Invention

This invention relates to the radiation therapy applied to patients who are typically treated for cancer or other ailments with high energy x-rays from medical linear accelerators.

The invention is directed to a method and system to reconstruct the dose the patient has received using as input the radiation fields measured during treatment on the exit side of the patient with an imaging system capable of integration or a radiation detector array. This information may be used as a quality control measure of the treatment to avoid errors by comparing the reconstructed dose to the intended planned dose.

2. Prior Art

U.S. Pat. No. 5,754,622 describes a system for verifying the amount of radiation delivered to an object. However, this system does not describe the method to accomplish a reverse calculation. In particular, there are several problems not addressed. Radiation absorbed in the patient will cause scatter radiation, some of which will strike the imaging device (3) adding to the signal recorded. Some imaging devices are very energy dependent and will over respond to the scattered radiation. The spectrum of the x-rays traversing through the patient will change as some energies of the spectrum are differentially absorbed and scatter by the patient more than other energies in the spectrum. The imaging device (3) may respond differently to the rays (4) having traversed through different thicknesses of the body (22) because of the change in spectrum along the different ray paths. Not accounting for these effects can lead to uncertainties of such magnitude as to yield the final reconstructed dose to be of no practical use.

U.S. Pat. No. 6,438,202 describes a method using a post-patient radiation monitor to verify the entrance radiation and delivered dose. However, this method also does not describe a way to account for the sources of error due to scatter from the patient and an energy dependent detector.

U.S. Pat. No. 6,636,622 describes a method to verify the radiation treatment using the exit-transit dose images. The method described is an iterative process for deriving the primary fluence from the exit images. This process is entirely different from the present invention that does not use an iterative process. The present invention is a different method for arriving at the primary fluence from an exit image. For example, the scatter component of the exit image is never explicitly computed, but accounted for from measured data used in the method.

Methods for reconstructing the dose to the patient from exit images have also been described in the literature. A publication not related to the above cited patents is: Markus Wendling, Robert J. W. Louwe, a Leah N. McDermott, Jan-Jakob Sonke, Marcel van Herk, and Ben J. Mijnheer, "Accurate two-dimensional IMRT verification using a back-projection EPID dosimetry method," Med. Phys. 33, 259-273 (2006), and Markus Wendling, Leah N. McDermott, Anton Mans, Jan-Jakob Sonke, Marcel van Herk, and Ben J. Mijnheer, "A simple backprojection algorithm for 3D in vivo EPID dosimetry of IMRT treatments," Med. Phys. 36, 3310-3321 (2009). The two reports also uses a series of EPID images for different field sizes and thicknesses as in the present invention, which in the reports is used to estimate an attenuation coefficient and a beam hardening coefficient in a fairly complicated process that is difficult to understand because the report is vague about some steps. Their method performs some conversions on the exit images and the dose to the patient is computed in a back projection algorithm. Whereas the invention here, while using some of the same input data, describes a method to convert the exit image directly to an in air x-ray intensity fluence map, and the dose to the patient is then computed from the in air fluence map using a forward dose algorithm in the same manner typically used in treatment planning systems.

In W D Renner, K Norton, T Holmes, "A method for deconvolution of integrated electronic portal images to obtain incident fluence for dose reconstruction," JACMP 6, 22-39 (2005), a method is described for converting images of the treatment field taken with an image detector without the patient being there to in air x-ray intensity fluence maps, which are then used to compute the dose to the patient. The method can only be used to reconstruct the dose to the patient from images taken without the patient being there, or from a measurement of the radiation field before it intersects the patient. The method cannot be used to estimate the dose to the patient from measurement of the beam that exits from the patient.

SUMMARY OF THE INVENTION

An object of the invention is to provide for converting the exit images (5) taken during patient treatment to an in air x-ray (or other radiation) intensity fluence map (14) which are of a form that can then be employed to compute the dose to the patient using a dose computation system.

These and other objects are attained in a method and system for determining a treatment dose delivered to a patient during radiation therapy based on integrated exit-transit images captured there from. In accordance with the method and system, a plurality of reference exit images are established. These reference exit images are measured by a radiation detector array for a range of treatment field sizes and a range of water equivalent phantom thicknesses emulating a patient. For each of the phantom thicknesses, a point spread kernel is determined for converting the radiation exit-transit images to corresponding in air radiation intensity fluence maps, with each in air radiation fluence map being indicative of an input radiation dose to the phantom, resulting in a plurality of reference point spread kernels. The radiation detector array is used to capture a plurality of integrated exit images for a plurality of the treatment fields upon a patient during radiation therapy of the patient, such that each integrated exit image includes a plurality of pixels defined with respect to the radiation detector array. The pixels each have an integrated pixel value associated therewith. There is defined for each pixel of the integrated exit images at least one water equivalent path representing a path traversed through the patient by a ray of radiation passing from a source to said pixel, the water equivalent path being calculated based upon image data established for the patient. At least one point spread kernel value is then interpolated from a plurality of reference point spread kernels for each pixel based on the water equivalent path. Deconvolution is performed on the patient exit images using the point spread kernel derived from the plurality of reference point spread kernels, whereby an in air radiation intensity fluence map indicative of the dose delivered to the patient is determined based on the exit images.

DETAILED DESCRIPTION OF THE PREFERRED EMBODIMENTS

Figure 1:
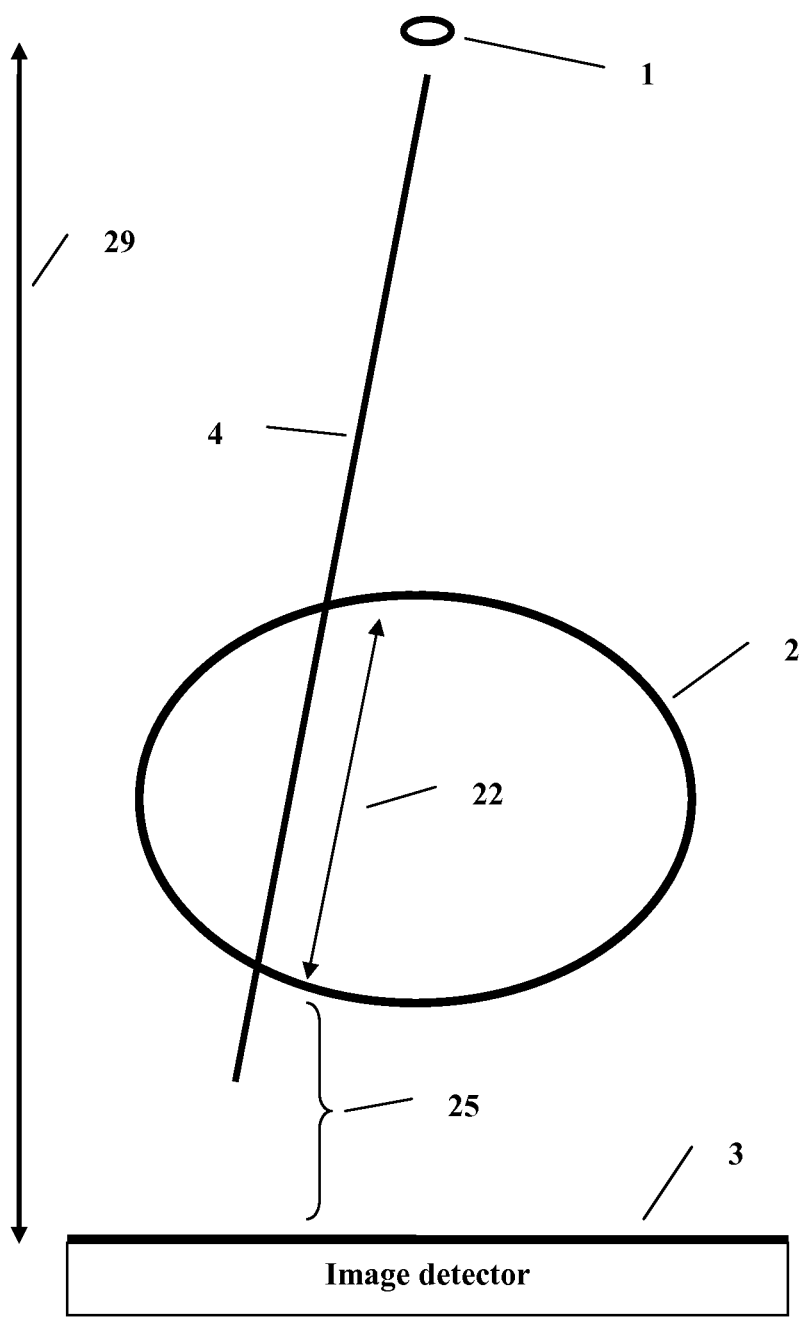
FIG. 1 is a schematic diagram illustrating an exemplary setup for measuring an exit image during patient treatment in accordance with one aspect of the present invention.

Drawing Reference Numerals 1 the source of x-rays.
2 the patient.
3 the image detector.
4 the ray from the source of x-rays to the image detector.
5 the exit image captured by the image detector.
6 the deconvolution of the image (5) to an intermediate image (7) using a kernel derived for a fixed phantom thickness (26), and in a further embodiment for a fixed source to image detector distance (24) or phantom to image detector distance (23).
7 the intermediate image produced from the exit image (5) by deconvolution with a kernel (6).
8, 10, 12 the convolution of the image (5) to intermediate images (9, 11, 13) using the succeeding steps in thickness from the available kernels.
9, 11, 13 the intermediate images produced from the deconvolution of the input exit image (5) as described above.
14 the final output image which is the in air x-ray intensity fluence map to be used to compute the dose to the patient using a dose algorithm.
15, 16 two corresponding pixels from two intermediate images that bracket the water equivalent thickness traversed through the patient (22) to reach the corresponding pixel (19) in the exit image (5). In a further embodiment the interpolation would include another dimension for intermediate images with source to image distance (24) that bracket the source to image distance (29), or the air gap distance (23) that brackets the air gap (25).
17 interpolation of the input pixel values (15) and (16) to produce a final pixel value (19) in the final image (14).
19 the final pixel value interpolated between the corresponding pixel values (15) and (16).
20 the water equivalent phantom used to generate the data to fit point spread kernels for a range of phantom thicknesses (26). In a further embodiment to include different source to image distances (24) or air gap distances (23).
21 a collimated field size.
22 the water equivalent path through the patient (2) along a ray from the x-ray source (1) that intersects the imaging device (3).
23 the air gap distance from the phantom (20) to the image detector (3).
24 the distance from the x-ray source (1) to the image detector (3) for the reference image.
25 the distance from the exit surface of the patient (2) to the image detector (3).
26 the water equivalent thickness of the phantom (20).
27 narrow collimated field size.
28 ion chamber with build up cap.
29 the distance from the x-ray source (1) to the image detector (3) for the patient exit image.
40 medical accelerator.
41 patient support system on which the patient lies.
42 data measured to characterized the image detector response to different thickness of water equivalent material and for different source to image distances (24) and different air gap distances (23).
43 process of generating point response kernels for each thickness (26), source to image distance (24) and air gap distance (23).
44 method detailed in FIGS. 3 and 6 to convert patient exit images to in air x-ray intensity fluence maps.
45 computerized tomography images that are used to model the patient's body.
46 computation system that will compute the dose to the patient given an in air x-ray intensity fluence map for each treatment beam.
47 system that displays the dose computed to the patient to the practitioner.
50 part of flow chart of method, beginning of loop to process each exit image from the patient treatment.
51 part of flow chart of method, process of ray tracing the path through the patient model for each pixel on the exit image.
52 part of flow chart of method, decision on whether to correct pixel data for attenuation by the patient, based on whether the reference kernels were fitted with the data.
53 part of flow chart of method, correct pixel values by division by the attenuation of the ray reaching that pixel.
54 part of flow chart of method, process of searching the exit image to determine the maximum thickness that needs to be accounted for, to save computer time in the next step of (55).
55 part of flow chart of method, for each point spread kernel developed from the reference images, do a deconvolution process to produce an intermediate image.
56 part of flow chart of method, the process of interpolation among the intermediate images to produce a final image that represents an in air x-ray intensity fluence map.
57 part of flow chart of method, the process of computing the dose to the patient using the final images.

FIG. 1 illustrates a geometry for which an exit image is obtained during patient treatment. Rays (4) from the source of x-rays (1) travel through the patient (2) along a path (22) to arrive at the image detector (3) where the intensity of the radiation is recorded along with any radiation scattered in the patient (2) that might also reach the image detector (3).

Figure 2:
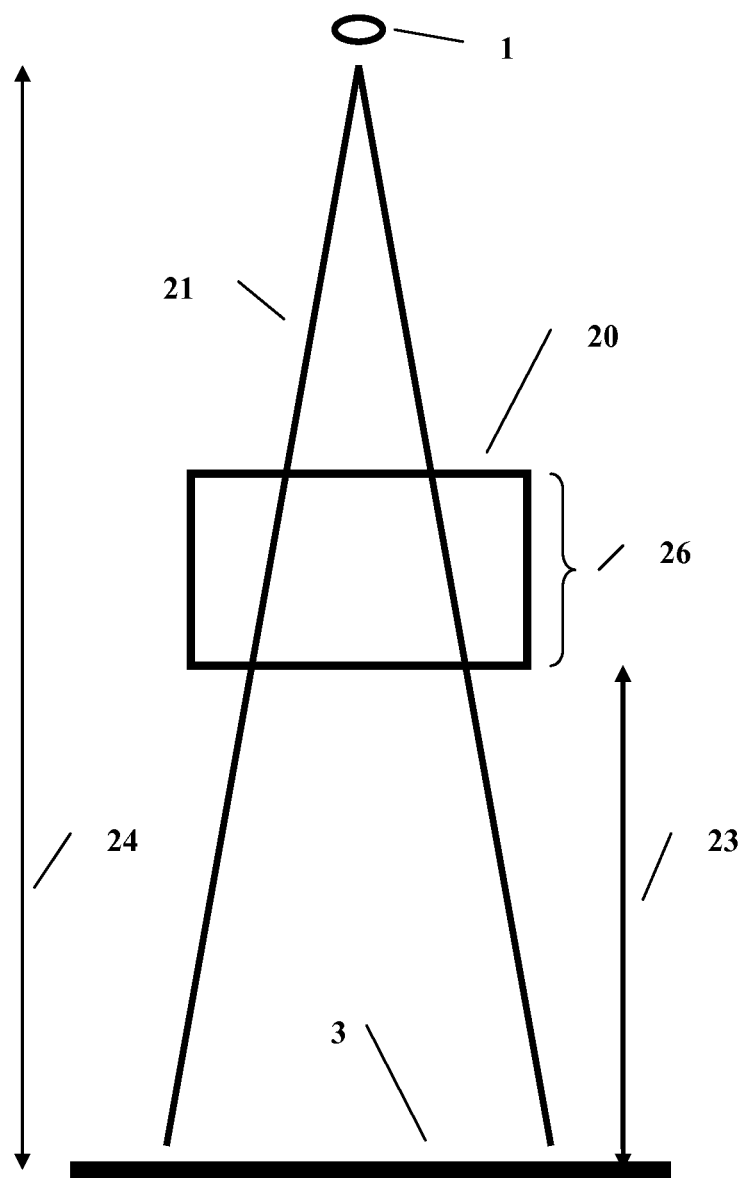
FIG. 2 is schematic diagram illustrating an exemplary setup for acquiring reference image data in accordance with another aspect of the present invention.

FIG. 2 illustrates a geometry employed to measure the data needed to implement the method. A uniformly thick water equivalent phantom (20) is placed in the beam of a radiation field collimated to a known field size (21) between the source of x-rays (1) and the image detector (3). Images are captured for a range of field sizes (21), phantom thicknesses (26), source to image detector distance (24), and air gap distance (23).

Figure 3:
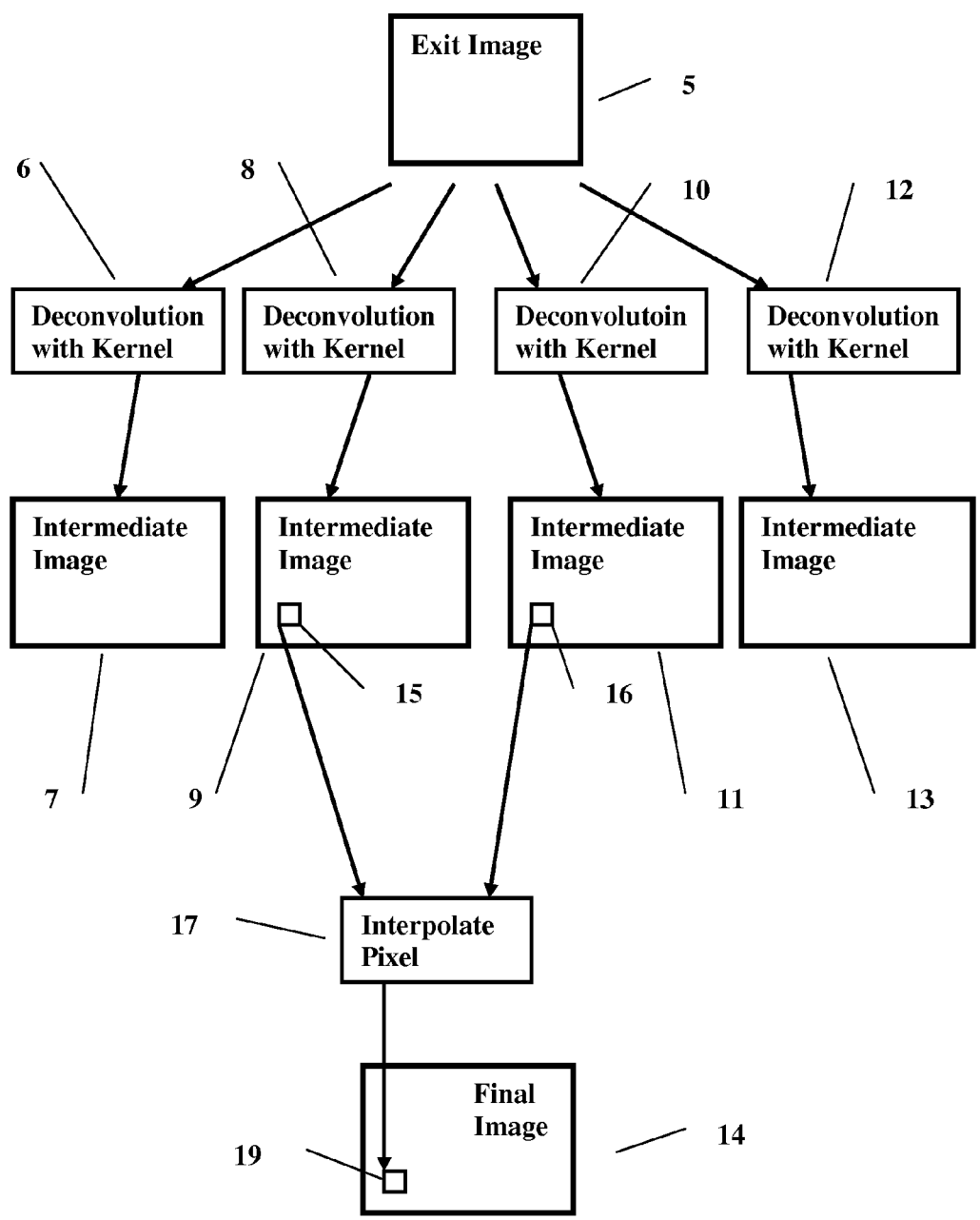
FIG. 3 is a schematic diagram illustrating a flow of processes in an exemplary embodiment of the present invention.

FIG. 3: illustrates the method in the preferred embodiment. The input exit image (5) measured with the radiation detector (3) is converted by a process of deconvolution (6, 8, 10, 12) to intermediate images (7, 9, 11, 13), showing in the drawing four of a multiplicity of such images and conversions, using a look up table of point spread kernels generated from a measurement of phantom thicknesses (26) for a range of field sizes (21) and which in a further embodiment of the method may be also be indexed by source to detector distance (24) or alternately the air gap distance (23). The final image (14) is produced by interpolation for the same corresponding pixels (15, 16) in the corresponding images (9, 11) that bracket the water equivalent path through the patient (22), and in a further embodiment of the invention would also carry out an interpolation (17) between such intermediary images that bracket the source to image detector distance (29) or air gap distance (23) of the exit image pixel.

Figure 4:
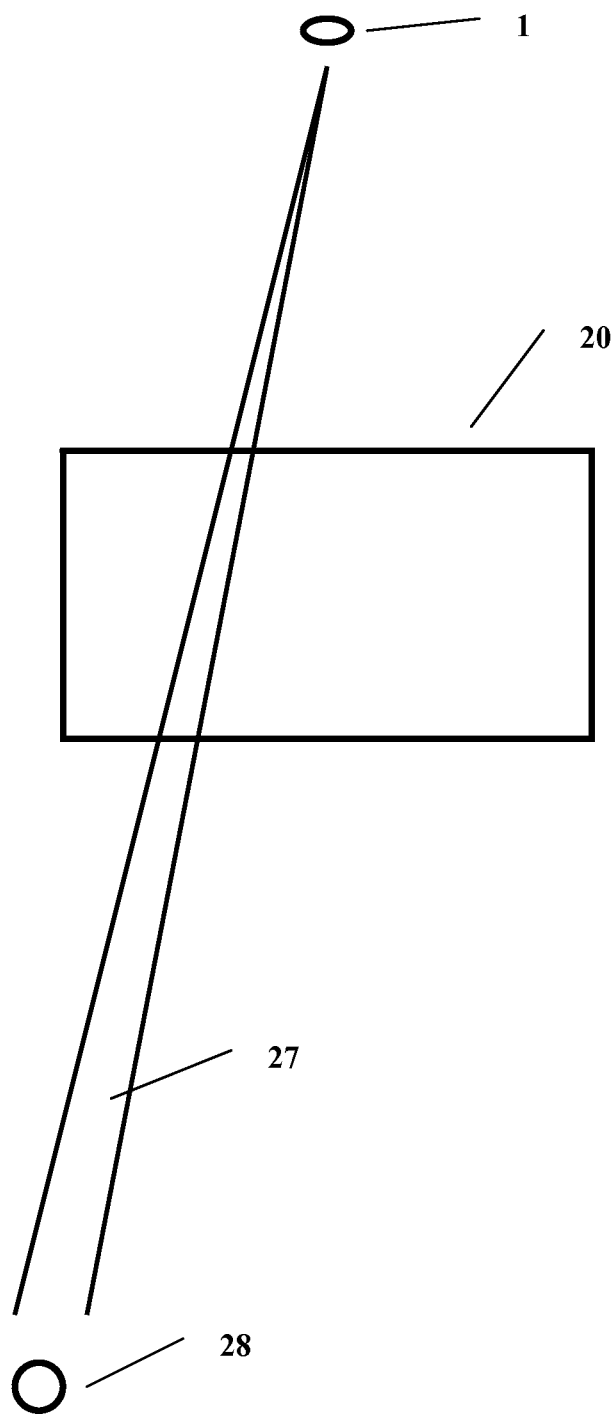
FIG. 4 is schematic diagram illustrating an exemplary setup for measuring narrow beam transmission through a water equivalent phantom in accordance with yet another aspect of the present invention.

FIG. 4: illustrates a geometry for measuring narrow beam transmission through a water equivalent phantom (20).

Figure 5:
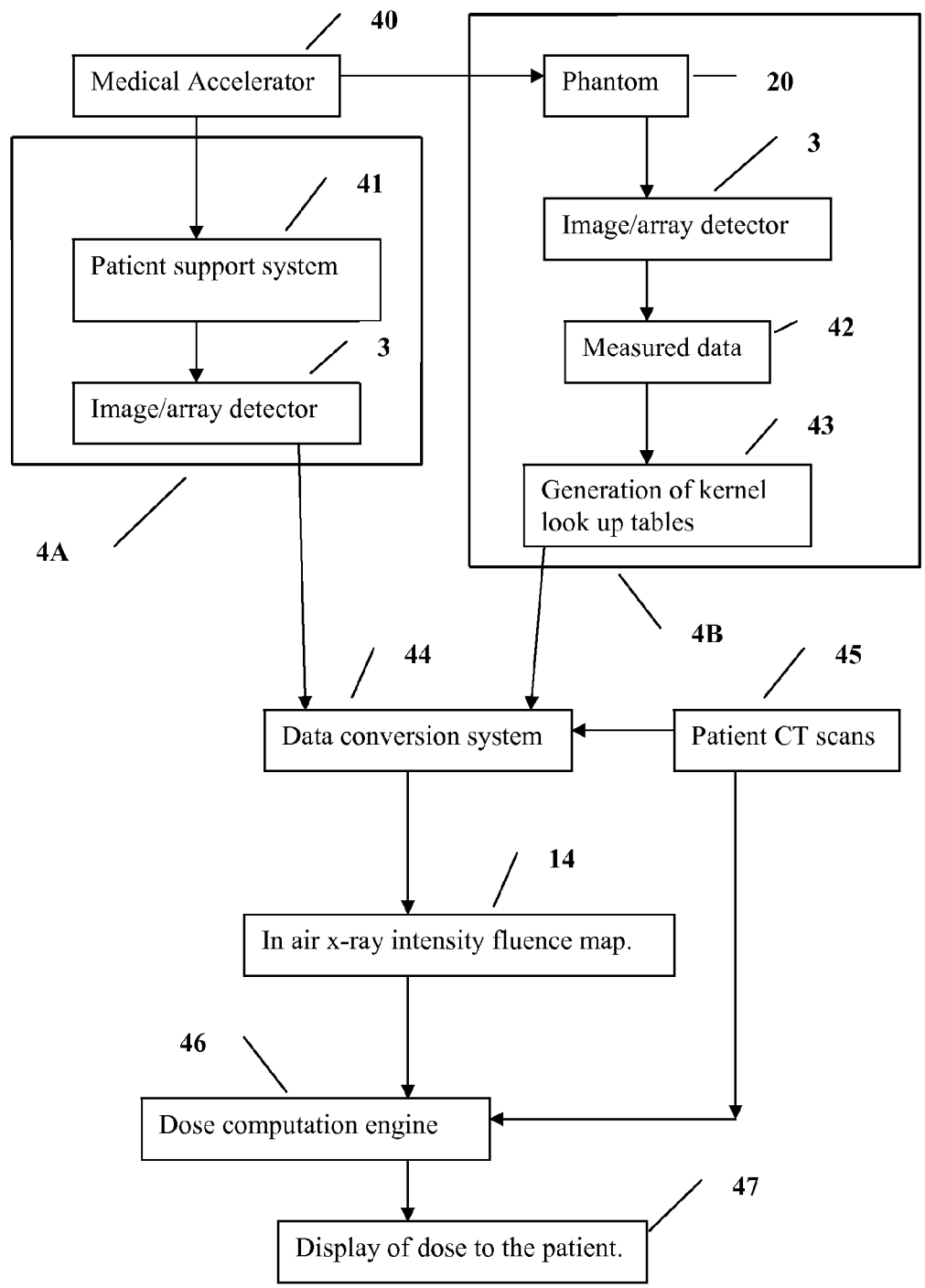
FIG. 5 is a block diagram illustrating a system formed in accordance with one exemplary embodiment of the present invention.

FIG. 5 illustrates the block diagram of the operational intercoupling of functional units in a system formed in accordance with one embodiment of the present invention. The system generally includes a radiation treatment imaging portion 4A and a reference data acquisition portion 4B. The radiation treatment portion 4A includes a suitable medical accelerator (40) which is used both to generate data described below (in portion 4B), and to generate the patient exit images (in portion 4A) in forming in air radiation intensity fluence maps (preferably, in air x-ray intensity fluence maps) that are used for computation. When used with the radiation treatment imaging portion 4A, the medical accelerator (40) is coupled to a patient support system (41) on which the patient lies during a treatment session. An image/array detector (3) is suitably disposed relative to the patient support system (41) to capture exit images during treatment, created by the radiation received from the medical accelerator (40) upon passage through and about the patient.

When used for the reference data acquisition portion 4B, the medical accelerator (40) is operably coupled and employed with the image/array detector (3) (preferably the same detector (3) employed in portion 4A) during a non-treatment, reference data acquisition process as described herein. A reference data measurement unit (42) is employed with the medical accelerator (4) and image/array detector (3) to characterize the image detector response to different thickness of water equivalent material (20) and for different source to image distances (24) and different air gap distances (23) (as illustrated in FIG. 2). A processing unit (43) executes a process of generating point response kernels for each thickness (26), source to image distance (24), and air gap distance (23).

Preferably, the reference data measurement unit (42) is employed in advance of patient treatment to make the measured data available for reference, so that prompt dosage information may be generated and fed back to the user/patient as necessary. Once the image/array detector (3) has acquired the radiation data from (or during) a treatment session, a data conversion system (44) applies to the acquired data the appropriate kernel information retrieved from corresponding look-up tables or the like.

The measured data obtained by the reference data measurement unit (42) is used to generate point spread kernels. The data conversion system (44) uses the point spread kernels to convert the patient exit images to in air x-ray intensity fluence maps (14). In doing so, the data conversion system (44) takes into account CT scans or other computerized tomography images (45) available to model the patient's body (or the water equivalent path that a ray of radiation would traverse through the patient to reach particular parts of the image/array detector (3)).

The resulting in air x-ray intensity fluence maps (14) are input to a dose computation engine (46) that computes the dose to the patient given the in air x-ray intensity fluence map corresponding to each treatment beam. A display system (47) then displays the computed dose to the patient and/or to the practitioner.

Figure 6:
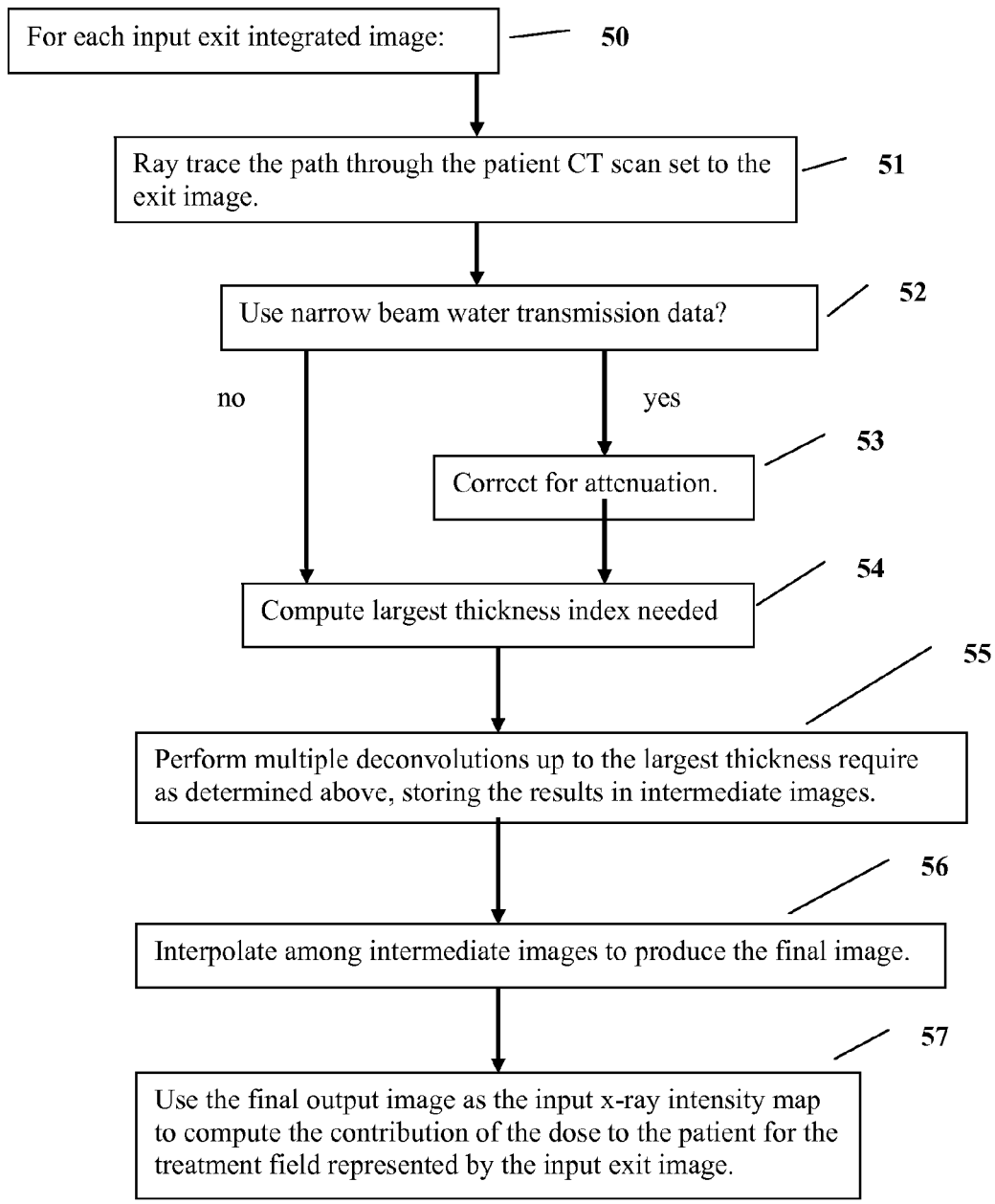
FIG. 6 is a flow diagram illustrating a flow of steps executed by a portion of the system embodiment shown in FIG. 5; and, FIG. 7 is a schematic diagram illustrating a graphic plot of a curve fitted to characterize variation of a signal value with air gap variation.

FIG. 6 illustrates the data flow of in an exemplary method established in accordance with the embodiment illustrated in FIG. 5.

The different functional units may be implemented using any suitable measures known in the art. For example, the data conversion system, dose computation engine, and other such units may be programmably implemented in one or more microprocessor based platforms served by suitable memory for data access and storage.

It is known in the art that the point response of an electronic portal imaging device (EPID) can be represented by a sum of exponentials:

$$k(r) = \sum_{i}^{n} a_i e^{-b_i r}$$

where k(r) is the point spread response, r is the radius in cm of a point from a ray, $a_i$ and $b_i$ are parameters for one of n exponentials. In the preferred embodiment the value of n is five. This information was made use of to develop a method to fit the point response parameters $a_i$ and $b_i$ from a series of open field size (21) measurements with an electronic portal imaging device (EPID) or any image or radiation array detector technology (3). The parameters of the sum of exponentials are fitted as a model so that a deconvolution with the model produces the effective in air x-ray intensity fluence map from which the correct dose is computed. If the measured image $I_{image}$ is a result of a convolution of the input x-ray intensity fluence map $I_{fluence}$ with the point response k(r), then we have mathematically for $I_{image}$:

$$I_{image} = I_{fluence} \otimes k(r)$$

where the symbol ⊗ designates convolution. Then the fluence can be recovered by a deconvolution process. Using the convolution theorm, $I_{image}$ is the inverse Fourier transform of the Fourier transform of $I_{fluence}$ times the Fourier transform of k(r). Because of circularly symmetry, the two dimensional Fourier transform of k(r), namely K(q), can be given by the one dimensional Hankel transform of k(r):

$$K(q) = \sum_{i}^{n} a_i \frac{2\pi b_i}{(4\pi^2 q^2 + b_i^2)^{3/2}}$$

where q is spatial frequency in cycles per cm.

Therefore we have by the convolution relationship:

$$F(I_{image}) = F(I_{fluence}) F(k(r)) = F(i_{fluence}) K(q)$$

Once we have broken $I_{image}$ out into its spatial frequency components, we can perform a deconvolution by dividing the spatial frequency components by K(q) to cancel it out, where we then have the result:

$$F^{-1}(F(I_{fluence})K(q)/K(q))=F^{-1}(F(I_{fluence}))=I_{fluence}$$

However, in reality $I_{fluence}$ cannot be fully recovered because k(r) is a low pass operation, and spatial frequencies attenuated to noise levels and lower cannot be recovered by an inverse operation. The deconvolution process is than an approximation.

In accordance with an aspect of the present invention, the disclosed method extends the known approach for determining the dose to the patient from images taken before the patient, to images taken after the patient is in place (in situ), by fitting a series of point spread response kernels for different thicknesses (26) of intervening water equivalent phantoms (20) using the images captured by the image detector (3). The image detector is preferably any array of radiation detectors capable of measuring the radiation, and the structural details of such physical device is not part of this invention. Typical available devices are electronic portal imaging devices, ion chamber arrays, and diode arrays.

A range of field sizes (21) are imaged. An example set of field sizes (21) (in cm) would be 4×4, 6×6, 10×10, 12×12, 16×16, 20×20, and 25×25. The fields need not be square but could be rectangular or any shape for which an output factor can be measured or determined. The exact number and field sizes used may vary but in general should cover the practical range of field sizes that can be used with the image detector. Each field size will correspond to a sampling from the spatial frequency space in the frequency domain necessary for the fitting of parameters using the frequency domain as illustrated above.

A purpose here is to cover as much as possible the range of spatial frequencies encountered in clinical treatment fields. For each field size used, the dose in water or equivalent material must also be measured and known for some set distance to the water surface, depth, and monitor unit setting on the treatment machine. The phantom scatter factor is computed using a dose algorithm, and divided into the measured dose to determine an effective collimator scatter factor of the field for some point in the field area. The kernel is fitted so as to produce this factor for each of the input fields using, for example, least squares. The kernel will then necessarily convert the exit image back to in air x-ray intensity fluence as it is fitted to produce that result.

For the set of field sizes (21), images are captured for different thickness (26) of an intervening water equivalent phantom (20). An example of thicknesses (26) used would be 0, 5, 10, 15, 20, 25, 30, 35, 40, 45, 50, 55, and 60 cm of water or water equivalent material but the actual choice in thicknesses to use can vary. As interpolation is preferably used (as described below) between thicknesses, the increment in thickness is suitably set to minimize interpolation error.

Referring to FIG. 2, in a preferred embodiment of the invention, the image detector (3) is positioned at a source to image detector distance (SID) (24) that will be used for imaging the patients, and for each thickness of solid water (26) the mid-thickness is placed at isocenter of the machine. By holding the image detector to a fixed distance (24) and centering the phantom (20) about isocenter, one data set can be used as an approximation for all expected situations without having to consider different air gap distances (25) between the patient and the detector, as the change in the scatter contribution is known to be a slow function of the air gap. However, another embodiment of the invention would be to repeat the measurements at different source to detector distances (24) or air gap distances (23) to enable a further refinement in the method to be described below.

For each given thickness (26), the series of images taken for the different field sizes (21) are used to fit a point spread function (kernel), indexed by that thickness. Notice that this series of different thicknesses will include the zero thickness, such as used in the prior art for pre-treatment images. The images for each thickness are all normalized to a calibration image taken with zero thickness. The calibration image is for a monitor unit exposure and field size for which a definition of the monitor unit is known in terms of distance to phantom surface, depth, and dose rate in terms of cGy/mu (centiGray per monitor unit). The point spread for each thickness is fitted so that the value on the central axis of the radiation field is converted to the expected effective collimator scatter factor for the particular open field size when doing a deconvolution of the image with the fitted point spread function. The effective collimator scatter factor is computed by dividing the measured output factor in cGy/mu by the computed phantom scatter factor for the same field size and depth. For each thickness (26), there is the result of the point spread function that can be used as a deconvolution kernel to transform the image back to an in air x-ray intensity fluence map (14). The resulting process of converting the image back to in air x-ray intensity fluence is therefore dependent on actually measured image data rather than a formal computational model as in prior art cited above.

The measured image for each thickness of intervening phantom will contain the effect of the scatter reaching the imager from the phantom, and any energy response of the imaging device due to both the scatter radiation and the beam hardening from traversing the phantom. This will tend to be specific to the distance (23) by which the imager is displaced from the phantom (20). However, we will accept any errors in the air gap (25) from the patient to the image detector being different in one embodiment of the invention. Because the scatter contribution is a slowly changing function of air gap, the errors are expected to be small.

As a further embodiment of the invention, the kernels may also be generated for different air gap distances (23) by generating more images with a different phantom (20) to image detector (3) distance (23) in FIG. 2, or with varying source to image detector distance (24).

As a further embodiment of the invention, we can consider the transmission of the beam off axis separately from the central axis. This is performed by first measuring narrow beam transmission as a function of off axis distance and water equivalent thickness as illustrated in FIG. 4. This data may be collected, for example, by placing an ion chamber (28) with a suitable build up cap (material added to the ion chamber to achieve electronic equilibrium) at a suitably large air gap distance from an intervening water tank or water equivalent material (20). A multi-leaf collimator may then be used to form a small field beam having a width (27) to progress along an axis, diagonal, or any radius, out to the corner of the largest field size available.

Alternatively, the data may be measured in an equivalent manner with a narrow column of water disposed between the ion chamber and source of x-rays, with the column shifted and the gantry rotated accordingly, so that there is only a narrow scattering volume, to measure the attenuation of succeeding off axis rays. In all cases, each measured column is preferably converted to the thickness along the slant path through the water and then fitted to a sum of exponentials. The fit is then used to compute the transmission for any given water equivalent thickness including any needed extrapolation, and linear interpolation is performed between columns of such data. In this manner the transmission of a beam at any angle with the central axis can be computed for any given equivalent water thickness.

The use of the above narrow beam transmission fit is not essential to the embodiment of the method, but can be employed to improve the accuracy of off axis results since the beam transmission through the patient occurring off axis tends to be less than that occurring on the central axis. Using the transmission data, each pixel of the above exit images is first corrected for transmission through the phantom before deconvolution by dividing the pixel value by the attenuation value. This correction could also be moved to after the deconvolution. Without the data, the exit image values are used directly and the attenuation will be accounted for from the deconvolution kernel. It is important that kernels fitted with the water transmission data be used with the water transmission data in converting exit images to in air x-ray intensity fluence maps. Care is taken not to use with the water transmission data kernels which were fitted without use of the data, as illustrated at step (53) in the flow chart of FIG. 6.

The combined point spreads for each thickness will give a deconvolution kernel as a function of radius indexed by thickness, k(r,th) where th is thickness, where interpolation between thicknesses can give a continuous function of thickness. For each thickness, a two dimensional Fourier transform of k(r,th), or a one dimensional Handel transform of k(r,th), will be K(q,th). To perform a deconvolution in the spatial domain, one would have to use the transform of 1/K(q,th).

By way of example, consider the processing of each input exit image in step (50) of the flow chart FIG. 6 captured by an image detector (3) during radiation therapy of a patient (2), the exit image being formed by an array of pixels. For each pixel in the exit image, the equivalent water thickness traversed by the ray from the source of x-rays (1) to that pixel is needed. Each ray through a model of the patient, which may be formed by the patient's corresponding CT data set, is traced to compute the water equivalent thickness traversed (22) for each pixel in the exit image. In step (51) of the flow chart of FIG. 6, rays are traced from the source of x-rays along a path through the patient CT scan set to the pixels of the input exit image. The equivalent water thickness found from the ray trace through the patient is stored for each pixel. To save computer processing time, a coarser matrix of pixels can be ray traced with interpolation between pixels.

At step (52) a check is made as to whether the deconvolution kernel was fitted using the in water transmission data. If so, the attenuation value of each of the above rays is computed using the equivalent water path, and the intensity value at each pixel of the exit image is divided by the attenuation value, as indicated in the correction step (53) of FIG. 6. If the deconvolution kernel was not fitted using the in water transmission data, the flow proceeds to step (54) described below in later paragraphs.

A deconvolution can then be performed, where for each pixel in the exit image the thickness traversed to reach that pixel is used as an index into the kernel value to be applied at that point in the mathematical integration process of deconvolution.

Such a kernel, however, is variant as it will depend upon the position of the deconvolution kernel relative to the image, and the convolution theorem cannot be applied. Therefore, the deconvolution cannot be adequately performed by multiplication in the frequency domain. Consequently, the fast Fourier transform would be of no use to transform images to the spatial frequency domain. This can pose a serious problem in computation time for image detectors with a large number of detectors. Exit images taken with an electronic portal imaging device after normalization to the calibration image may be reduced to a larger pixel size such as approximately 1 mm, which still may leave an image size of the order of 400×300 pixels. We would not want to lose the advantage of the high resolution available in some image detectors with any lower resolution. One millimeter is still small compared to typical pencil beam sizes of 2 to 5 mm often used for dose computation. The deconvolution in the spatial domain just described above required about 9 minutes on a 1.81 GigaHertz Intel based PC computer running Windows XP. A seven field intensity modulated radiation therapy (IMRT) case would require approximately one hour to transform the seven fields, and an intensity modulated arc therapy (IMAT) in a case with 72 images would require over ten hours.

A one dimensional convolution is of the order $n^2$, whereas the fast Fourier transform is of order ($n \log_2 n$). For two dimensional images a convolution is of order $n^4$ and the fast Fourier transform is of the order $(n \log_2 n)^2$. For a 512×512 array size, using the fast Fourier transform should be about 3236/2 (the division by two from transforming each way) times faster than a discrete convolution. In the preferred embodiment of the invention, the large computational time required for a discrete deconvolution in the spatial domain is eliminated by use of the following approximation, also illustrated in the flow chart of FIG. 6 and in the schematic diagram of FIG. 3.

It is assumed that there are n total thicknesses measured with the image detector resulting in n deconvolution kernels, indexed by the thickness. For a single exit image, the image is deconvolved n times for each of the n kernels using a fast Fourier transform to produce n intermediate images. There in fact is only a need to convert images up to the thickness that includes all the thicknesses traversed for a particular image, for increased efficiency. In an exemplary embodiment of the present invention, a search is made for the maximum water thickness among all the pixels of the exit image, as indicated at step (54) in FIG. 6. From the list of deconvolution kernels for different thicknesses (preferably sorted in order of increasing thickness starting at zero), the index number for the smallest thickness greater than the maximum thickness is computed. Let M be the index number.

At step (55), for each deconvolution kernel from zero thickness up to and including the index number M found above, a deconvolution operation is performed on the input exit image (5) (of FIG. 3). Each such output image is stored in a list of intermediate images (7, 9, 11, 13) indexed by the thickness of the deconvolution kernel used therefore.

This part of the method is schematically illustrated in FIG. 3. The exit image (5) is deconvolved with M thicknesses, only four of which are illustrated in FIG. 3 (6, 8, 10, 12) to produce M deconvolved intermediate images (7, 9, 11, 13), with four images of a multiplicity of such images shown in FIG. 3.

Referring back to FIG. 6, in step (56), for each pixel in the input exit image, the water equivalent thickness stored for that pixel is consulted, and the two intermediate images that bracket the thickness value are determined. The pixel value between the corresponding pixel in those two images (15) (16) is interpolated using the thickness values as the index. The interpolated value for the corresponding pixel (19) is stored in a final output image (14) such as shown in FIG. 3.

As an example to illustrate the interpolation part of the method in step (56), if the thickness traversed for a particular pixel (19) were to be 32.0 cm, then interpolate between the output images deconvolved with a thickness that bracket 32.0 cm. Let image (9) be from a 30 cm thickness kernel and image (11) from a 35 cm thick kernel. Then the pixel value (15) in the 30.0 cm thickness kernel and the corresponding pixel value (16) in the 35.0 cm thickness kernel are interpolated (17) to produce the value to assign to the corresponding pixel (19) in a single output image (14). Using this scheme, the time required to process the exit image to produce the in air x-ray intensity fluence image was reduced from 9 minutes to about 1.7 seconds on the same computer (including the time for the ray trace). As the image detector point spread decreases rapidly with radius, and the patient thickness will usually be slowly varying over the area of the image, this method is a reasonable approximation to an equivalent deconvolution in the spatial domain. In an alternate embodiment of the method, the ray trace can be done on a coarser grid with values interpolated in between nodes to same computer time.

In another embodiment, the above transmission data can be used to compute the attenuation from the water equivalent path computed through the patient. The pixel values are then corrected for this attenuation. This further step will allow correction for the x-ray penetration that is less for rays disposed farther from the central axis. The spectrum off axis changes with lower energy components and as a result the x-rays have an increased attenuation rate.

In another embodiment of the method, additional data can be taken at different image detector distances (24) or air gap distances (23) to produce further sets of kernels, indexed also either by detector distance or by air gap distance. These kernels will add another dimension to the kernels with a corresponding interpolation of intermediate images by source to image detector distance (29) or air gap (25) as the embodiment may be.

For example, let there be images of a series of uniform thickness phantoms as before with an air gap of 50 cm (23), with a point spread kernel fitted for each thickness. Let there also be a set with an air gap of 25 cm (23). By means of interpolation, there would result a kernel that is a function of thickness and air gap, namely: k(r,th,ag) where ag is the air gap. The corresponding transform would be K(q,th,ag). In the interpolation scheme of FIG. 3 and FIG. 6 for block (56), interpolation would also be performed for the air gap. In the above example, if in addition to a path of 32 cm to a pixel of an exit image, the air gap from the patient to the image detector was 42 cm for that pixel, the final pixel value would be interpolated among the four intermediate images deconvolved with the point spread kernels for thicknesses of 30 cm and 35 cm with the air gap of 50 cm, and the intermediate images deconvolved with the point spread for thicknesses 30 cm and 35 cm with the air gap of 25 cm. Similar embodiments would alternatively consider the source to image distance instead, or as well.

As indicated at step (57), the final output image (14) (of FIG. 3) is obtained to include an in air x-ray intensity map which is then used directly to compute the dose to the patient from the radiation field that created the exit image. Repeating this process for each treatment field, the composite dose from all treatment fields to the patient is computed. For intensity modulated arc therapy (IMAT), the rotation is simulated by fixed treatment fields at the angles at which exit-transit images are captured. By capturing such images in small increments of angle, the resultant computed dose will be a good approximation.

In those embodiments of the method disclosed herein where additional data is taken (such as at different image detector distances (24) or air gap distances (23)) to produce further sets of kernels for geometries that deviate from isocenter of the patient, suitable air gap correction measures are preferably taken to correct for different exit surface distances to the given EPID. As noted in preceding paragraphs, a change in exposure to the EPID typically occurs as a slow function of the air gap distance (23) between the exit surface of the phantom (2) to the EPID (3). When the EPID (3) is used at the distance at which EPID images were taken to fit the EPID deconvolution kernel, errors due to the isocenter not actually being aligned with the center of the patient will be minimal.

The potential effects of such air gap 'errors' become more significant for larger fields sizes. A direct method is here described to correct for different air gap distances (25) due to either isocenter offset from the center of the patient, or use of the EPID (3) at a different distance (29). By normalizing data for each field size, differences are preferably employed rather than absolute values, so as to enhance accuracy and/or efficiency.

The variation of the EPID (3) signal with air gap distance (23) for a fixed field (21) and phantom thickness (26) is independent of the point response of the EPID (3) which is otherwise accounted for in the deconvolution process, as disclosed in FIG. 6. Hence, given a fixed field size (21) and thickness (26), the variation of signal with gap distance (23) may be measured and directly applied as a correction. This eliminates the need to execute a deconvolution with kernels measured for different air gaps and to then interpolate between those deconvolved images. Furthermore, signal variation versus air gap variation tends to yield a smooth curve which may be fitted to a second order polynomial and extrapolated to zero air gap distance (23). The scatter dose from the patient is governed by the inverse square law with the patient appearing as an extended source of radiation. The response of the EPID to the scatter radiation on the central axis is inherently accounted for when interpolation is made between the multiple output images from the deconvolution process (56). Extrapolation to larger air gaps may also be made until the minimum of the $2^{nd}$ order polynomial is reached, with the resulting value being used for larger air gaps as the curve flattens out with increased air gap distance.

This approach allows for a simple look up of a correction factor for the air gap differing from the nominal value for which the EPID deconvolution kernels were fitted, which is given by the equation:

$$\text{Air gap} = \text{EPID SID} - (100.0 \text{ cm} + 0.5 \times \text{thickness}),$$

where EPID SID (Source to Image Distance) is fixed (24) for all the images acquired for fitting the kernels, and isocenter is aligned with the center of the water phantom (26). Further, there is likely to be little variation between EPIDs (3) of the same model in terms of signal change with air gap change (23 and 25), and one set of data may be applied to numerous machines.

EPID images are captured for a fixed set of field sizes (21) and water thicknesses (26), with a variable range of air gaps (23). For each field size and thickness, a $2^{nd}$ order polynomial is fitted to the signal versus air gap distance curve, such that a fixed range of signals for air gaps starting at zero may be computed from the fit. A three dimensional air gap correction table indexed by field size, thickness, and air gap is directly generated from the data.

EXAMPLE

Application to Clinical Exit Images

The data in this example includes images taken for a range of thickness, field size, and air gap. On a pixel by pixel basis, given particular values of the air gap distance (25) and thickness (22) at a pixel, and a field size to be defined below, a correction factor is interpolated from the corresponding three dimensional air gap correction table and applied to that pixel value.

Clinical images, however, are not typically of square open field sizes. They tend to comprise modulated fields. The field size used to look up the correction factor must be generated by a suitable metric that accounts for the amount of scatter generated in the patient from the radiation field in such manner that different size square fields will generate different amounts of scatter. For each field image, the maximum intensity is determined, and all other pixels are divided by that maximum value. The pixels are then summed and multiplied by the area per pixel. A square root is then taken, and the result scaled (or, demagnified) as needed (such as to a distance of 100 cm). The field sizes used in the air gap table that is a function of air gap distance, thickness, and field size, are regenerated by this algorithm for consistency.

The air gap correction factor is the ratio of the result for the nominal air gap which the EPID kernels were generated with, divided by the result for the actual air gap in the clinical image at the particular pixel, and can be applied at step (56) in FIG. 6.

Figure 7:
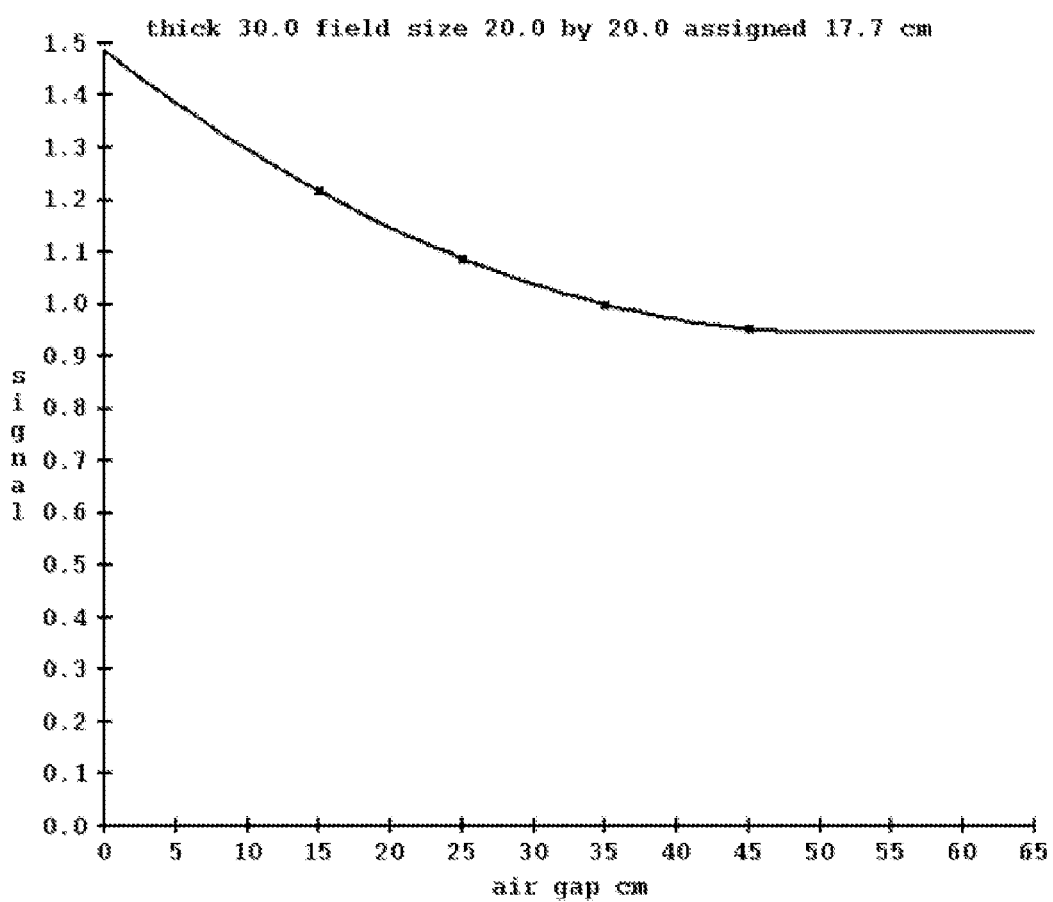

Turning more specifically to a quantitative example, for each field size and thickness, a $2^{nd}$ order polynomial is fitted to the central axis signal value versus air gap. The curve is extrapolated to zero field size and extended in the other direction. Once the minimum of the resulting parabolic curve is reached, the curve just extends at that minimum. FIG. 7 illustrates an exemplary plot of a sample curve for a 30 cm thick, 20×20 cm field size.

As noted, the field size is preferably generated by a suitable metric that will account for the amount of scattering from the radiation field since modulated fields are not open square and rectangular fields. For each field image, the maximum intensity is found, and all other pixels are divided by that maximum intensity. The pixels are then summed, multiplied by the area of an individual pixel. A square root is then taken, and the result scaled (or demagnified) to as needed, for instance to a distance of 100 cm. In the example of FIG. 7, an equivalent field size of 17.7 cm was computed for the image of a 20×20 cm field (demagnified to 100 cm). While something of a loose metric, this provides a common measure for all radiation fields.

For any given thickness, then, the curve is normalized to 1.0 for the air gap according to the equation:

Air gap cm=EPID SID cm−(100.0 cm+½×thickness)

For 30 cm thickness and 150 cm SID, the normalization is to an air gap of 35 cm. In application, the data is renormalized to whatever SID was used for the EPID kernel data. It is therefore preferable for the EPID kernel images be taken so that the above equation generates the correct air gap for a given thickness. On a pixel by pixel basis, given the air gap, thickness, and field size, a correction factor is interpolated from the corresponding three dimensional air gap correction table and applied to the given pixel value. Since the deconvolution has already accounted for the field size response of the EPID, the interpolated correction factor corrects for the change in intensity based on measured data due to change in air gap in the nominal measurement used to fit the exit EPID kernel.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. A method for determining a treatment dose delivered to a patient during radiation therapy based on integrated exit-transit images captured therefrom, comprising the steps of:
   establishing a plurality of reference exit images measured by a radiation detector array for a range of treatment field sizes and a range of water equivalent phantom thicknesses emulating a patient;
   determining for each of the phantom thicknesses a deconvolution kernel for converting the radiation exit-transit images to corresponding in air radiation intensity fluence maps, each in air radiation intensity fluence map being indicative of an input radiation dose to the phantom;
   capturing with the radiation detector array a plurality of integrated exit images for a plurality of the treatment fields upon a patient during radiation therapy of the patient, each integrated exit image including a plurality of pixels defined with respect to the radiation detector array, the pixels each having an integrated pixel value associated therewith;
   e. defining for each pixel of each integrated exit image at least one water equivalent path representing a path traversed through the patient by a ray of radiation passing from a source to said pixel, the water equivalent path being calculated based upon image data established for the patient; and,
   f. deconvolving each of the exit-transit images with at least one said deconvolution kernel to generate a corresponding in air radiation intensity fluence map for determining the delivered dose to the patient;
   wherein a plurality of intermediate in air radiation intensity fluence maps are generated from a plurality of said deconvolution kernels; and, a plurality of said deconvolution kernels are determined for each water equivalent phantom thickness from measurement at different air gap distances between the water equivalent phantom to the radiation detector array.

2. The method as recited in claim 1, wherein the in air radiation intensity fluence map at least at one pixel thereof is interpolated between said intermediate in air radiation intensity fluence maps, the interpolation being indexed by the water equivalent paths corresponding to the intermediate in air radiation intensity fluence maps of said pixel.

3. The method as recited in claim 2, further comprising computing a treatment dose based on the in air radiation intensity fluence map corresponding to each radiation treatment beam applied to the patient during the radiation therapy.

4. The method as recited in claim 2, wherein:
   the image data established for the patient is obtained as computerized tomography images modeling an anatomic portion of the patient; and,
   air gap correction is executed to alleviate error due to geometric offset in air gap between the patient and phantom, said air gap correction being applied to at least one pixel of an integrated exit image deconvolution;
      said air gap correction including generation of a gap correction factor applied to an integrated exit image deconvolution based on one said deconvolution kernel obtained for a phantom spaced by a predetermined nominal air gap distance from the radiation detector array, the gap correction factor being variable with the air gap offset between the patient and phantom;

the gap correction factor being defined according to a ratio of the predetermined nominal air gap distance and an actual air gap distance of the patient, the gap correction factor being selectively determined in value based upon a plurality of predetermined gap correction factor values derived for said deconvolution kernel;

the plurality of predetermined gap correction factor values being defined for at least one preselected combination of treatment field size and water equivalent phantom thickness, as points along a second order polynomial curve fitted to a plot of relative signal values measured by the radiation detector array for a central axis of the phantom as a normalized function of air gap distance, the gap correction factor value for a pixel of the integrated exit image deconvolution being selected according to a value of air gap distance corresponding to the pixel.

5. A system for determining a treatment dose delivered to a patient during radiation therapy based on integrated exit-transit images captured therefrom, comprising:

a radiation source;

a reference data acquisition portion operably coupled to said radiation source for establishing a plurality of reference exit images measured by a radiation detector array for a range of treatment field sizes and a range of water equivalent phantom thicknesses emulating a patient, said reference data acquisition portion determining for each of the phantom thicknesses a deconvolution kernel;

a radiation treatment imaging portion operably coupled to said radiation source, said radiation treatment imaging portion capturing with the radiation detector array a plurality of integrated exit images for a plurality of the treatment fields upon a patient during radiation therapy of the patient, each integrated exit image including a plurality of pixels defined with respect to the radiation detector array, the pixels each having an integrated pixel value associated therewith; and, a data conversion system coupled to said reference data acquisition and radiation treatment imaging portions for converting the radiation exit-transit images to corresponding in air radiation intensity fluence maps, each in air radiation fluence map being indicative of an input radiation dose to the phantom, said data conversion system being configured to:

define for each pixel of each integrated exit image at least one water equivalent path representing a path traversed through the patient by a ray of radiation passing from a source to said pixel, the water equivalent path being calculated based upon image data established for the patient; and, deconvolving each of the exit-transit images with at least one deconvolution kernel to generate said in air radiation intensity fluence maps;

wherein the data conversion system is programmably configured to generate a plurality of intermediate in air radiation intensity fluence maps from a plurality of selected deconvolution kernels; a plurality of the deconvolution kernels being determined for each water equivalent phantom thickness from measurement at different air gap distances between the water equivalent phantom to the radiation detector array.

6. The system as recited in claim 5, wherein the data conversion system is programmably configured to interpolate between said intermediate in air radiation intensity fluence maps to obtain the in air x-ray intensity fluence map at least at one pixel thereof, the interpolation being indexed by the water equivalent paths corresponding to the intermediate in air radiation intensity fluence maps of said pixel.

7. The system as recited in claim 6, further comprising a dose computation portion coupled to said data conversion system, said dose computation portion computing the treatment dose based on the in air radiation intensity fluence map corresponding to each radiation treatment beam applied to the patient during the radiation therapy.

8. The system as recited in claim 6, wherein:

the image data established for the patient is obtained by the data conversion system as computerized tomography images modeling an anatomic portion of the patient; and, the data conversion system executes air gap correction for alleviating error due to geometric offset in air gap between the patient and phantom, said air gap correction being applied to at least one pixel of an integrated exit image deconvolution;

said air gap correction including generation of a gap correction factor applied to an integrated exit image deconvolution based on one said deconvolution kernel obtained for a phantom spaced by a predetermined nominal air gap distance from the radiation detector array, the gap correction factor being variable with the air gap offset between the patient and phantom;

the gap correction factor being defined according to a ratio of the predetermined nominal air gap distance and an actual air gap distance of the patient, the gap correction factor being selectively determined in value based upon a plurality of predetermined gap correction factor values derived for said deconvolution kernel;

the plurality of predetermined gap correction factor values being defined for at least one preselected combination of treatment field size and water equivalent phantom thickness, as points along a second order polynomial curve fitted to a plot of relative signal values measured by the radiation detector array for a central axis of the phantom as a normalized function of air gap distance, the gap correction factor value for a pixel of the integrated exit image deconvolution being selected according to a value of air gap distance corresponding to the pixel.

9. A method for determining a treatment dose delivered to a patient during radiation therapy based on integrated exit-transit images captured therefrom, comprising the steps of:

establishing a plurality of reference exit images captured by a radiation detector array for a range of treatment field sizes and a range of water equivalent phantom thicknesses emulating a patient, the phantom being spaced by an air gap from the radiation detector array;

determining for each of the phantom thicknesses a deconvolution kernel for converting the radiation exit-transit images to corresponding in air radiation intensity fluence maps, each in air radiation intensity fluence map being indicative of an input radiation dose to the phantom;

capturing with the radiation detector array a plurality of integrated exit images for a plurality of the treatment fields upon a patient during radiation therapy, each integrated exit image including a plurality of pixels defined with respect to the radiation detector array, the pixels each having an integrated pixel value associated therewith;

defining for each pixel of each integrated exit image at least one water equivalent path representing a path traversed through the patient by a ray of radiation passing from a source to said pixel, the water equivalent path being calculated based upon image data established for the patient; and, deconvolving each of the integrated exit images with at least one said deconvolution kernel to generate a corresponding in air radiation intensity fluence map for determining the delivered dose to the patient.

10. The method as recited in claim 9, wherein the plurality of reference exit images include images captured for a range of distances between the source and the radiation detector array and for a range of distances for the air gap.

11. The method as recited in claim 9, wherein said deconvolution kernel is selected for deconvolution of each integrated exit image according to phantom thickness corresponding to the image data established for the patient, and at least one of a corresponding: field size, distance defined between the source and radiation detector array, and distance defined by the air gap.

12. The method as recited in claim 11, further comprising air gap correction for alleviating error due to geometric offset in air gap between the patient and phantom, said air gap correction being applied to at least one pixel of an integrated exit image deconvolution.

13. The method as recited in claim 12, wherein said air gap correction includes generation of a gap correction factor applied to an integrated exit image deconvolution based on one said deconvolution kernel obtained for a phantom spaced by a predetermined nominal air gap distance from the radiation detector array, the gap correction factor being variable with the air gap offset between the patient and phantom.

14. The method as recited in claim 13, wherein the gap correction factor is defined according to a ratio of the predetermined nominal air gap distance and an actual air gap distance of the patient, the gap correction factor being selectively determined in value based upon a plurality of predetermined gap correction factor values derived for said deconvolution kernel.

15. The method as recited in claim 14, wherein the plurality of predetermined gap correction factor values are defined for at least one preselected combination of treatment field size and water equivalent phantom thickness, as points along a polynomial curve fitted to a plot of relative signal values measured by the radiation detector array for a central axis of the phantom as a normalized function of air gap distance, the gap correction factor value for a pixel of the integrated exit image deconvolution being selected according to a value of air gap distance corresponding to the pixel.

16. The method as recited in claim 15, wherein the polynomial curve is a second order polynomial curve normalized according to the equation:

$$\text{Air gap} = \text{EPID SID} - (100.0 + \tfrac{1}{2} \text{ thickness})$$

wherein Air gap represents the air gap distance value where the polynomial curve indicates the relative signal value to be approximately 1.0; EPID SID represents the distance defined between the source and radiation detector array; and, thickness represents the phantom thickness.

17. The method as recited in claim 16, wherein:

a plurality of intermediate in air radiation intensity fluence maps are generated by deconvolution of the integrated exit image with a plurality of deconvolution kernels; and, the in air radiation intensity fluence map at least at one pixel thereof is interpolated between the intermediate in air radiation intensity fluence maps, the interpolation being indexed by the water equivalent paths corresponding to the intermediate in air radiation intensity fluence maps of said pixel.

18. The method as recited in claim 12, wherein:

the reference exit images are predefined relative to a fixed air gap distance between an exit surface of the phantom and the detector; and, the image data established for the patient includes a CT scan set captured for the patient.

19. The method as recited in claim 9, wherein an attenuation factor is applied to the pixel value to correct for the attenuation through the phantom or patient area, the attenuation factor being determined responsive to the water equivalent path determined for the pixel.

20. The method as recited in claim 9, wherein the radiation is of x-ray type, the method generating in air x-ray intensity fluence maps; the method further comprising computing a treatment dose based on the in air radiation intensity fluence map corresponding to each radiation treatment beam applied to the patient during the radiation therapy.

* * * * *